(12) United States Patent
Hyde et al.

(10) Patent No.: US 7,649,182 B2
(45) Date of Patent: Jan. 19, 2010

(54) VARIABLE MULTI-STAGE WAVEFORM DETECTOR

(75) Inventors: Roderick A. Hyde, Redmond, WA (US); Muriel Y. Ishikawa, Livermore, CA (US); Edward K. Y. Jung, Bellevue, WA (US); Nathan P. Myhrvold, Medina, WA (US); Clarence T. Tegreene, Bellevue, WA (US); Lowell L. Wood, Jr., Livermore, CA (US)

(73) Assignee: Searete LLC

( * ) Notice: Subject to any disclaimer, the term of this patent is extended or adjusted under 35 U.S.C. 154(b) by 0 days.

(21) Appl. No.: 12/218,923

(22) Filed: Jul. 18, 2008

(65) Prior Publication Data

US 2008/0302971 A1 Dec. 11, 2008

Related U.S. Application Data (63) Continuation-in-part of application No. 11/588,851, filed on Oct. 26, 2006, now Pat. No. 7,427,762, and a continuation-in-part of application No. 12/077,441, filed on Mar. 18, 2008, and a continuation-in-part of application No. 12/079,735, filed on Mar. 28, 2008, and a continuation-in-part of application No. 12/215,064, filed on Jun. 24, 2008, and a continuation-in-part of application No. 12/215,155, filed on Jun. 24, 2008, and a continuation-in-part of application No. 12/218,226, filed on Jul. 10, 2008.

(51) Int. Cl.
*G01J 1/42* (2006.01)

(52) U.S. Cl. .......................... 250/394; 250/395

(58) Field of Classification Search .......... 250/394, 250/395
See application file for complete search history.

(56) References Cited

U.S. PATENT DOCUMENTS

| | | | |
|---|---|---|---|
| 4,149,902 | A | 4/1979 | Mauer et al. |
| 4,254,330 | A | 3/1981 | Stauffer et al. |
| 4,804,848 | A | 2/1989 | Horiba et al. |
| 4,980,554 | A | 12/1990 | Ahn |
| 5,691,532 | A | 11/1997 | Hait |
| 5,777,326 | A | 7/1998 | Rockwood et al. |
| 6,180,415 | B1 | 1/2001 | Schultz et al. |
| 6,627,914 | B1 | 9/2003 | Komiyama et al. |
| 6,791,432 | B2 | 9/2004 | Smith et al. |
| 6,938,325 | B2 | 9/2005 | Tanielian |
| 6,958,729 | B1 | 10/2005 | Metz |
| 6,969,847 | B2 | 11/2005 | Davis et al. |
| 7,145,124 | B2 | 12/2006 | Garrood et al. |
| 7,180,065 | B2 | 2/2007 | Craig et al. |
| 7,232,999 | B1 | 6/2007 | Otten, III et al. |
| 7,391,032 | B1 | 6/2008 | Hyde et al. |
| 2001/0038325 | A1 | 11/2001 | Smith et al. |
| 2003/0002045 | A1 | 1/2003 | Nemat-Nasser et al. |
| 2003/0178548 | A1 | 9/2003 | Nishimoto et al. |
| 2004/0066251 | A1 | 4/2004 | Eleftheriades et al. |

(Continued)

OTHER PUBLICATIONS

PCT International Search Report; International App. No. PCT/US07/04400; Nov. 3, 2008; pp. 1-2.

(Continued)

*Primary Examiner*—David P Porta
*Assistant Examiner*—Mindy Vu (57) ABSTRACT

A variable waveform detector may include multiple stages.

28 Claims, 7 Drawing Sheets

U.S. PATENT DOCUMENTS

| | | | |
|---|---|---|---|
| 2004/0114203 A1 | 6/2004 | Batchko | |
| 2004/0184719 A1 | 9/2004 | Kiadeh | |
| 2004/0188617 A1 | 9/2004 | Devitt et al. | |
| 2004/0189528 A1 | 9/2004 | Killen et al. | |
| 2005/0070803 A1 | 3/2005 | Cullum et al. | |
| 2005/0073744 A1 | 4/2005 | Zheludev et al. | |
| 2005/0084268 A1 | 4/2005 | Weigert | |
| 2005/0098720 A1 | 5/2005 | Traynor et al. | |
| 2005/0107125 A1 | 5/2005 | Gilbert | |
| 2005/0134819 A1 | 6/2005 | de Jager | |
| 2005/0146402 A1 | 7/2005 | Sarabandi et al. | |
| 2005/0221128 A1 | 10/2005 | Kochergin | |
| 2005/0247337 A1 | 11/2005 | Chen et al. | |
| 2006/0022875 A1 | 2/2006 | Pidwerbetsky et al. | |
| 2006/0043297 A1 | 3/2006 | Ouvrier-Buffet et al. | |
| 2006/0049331 A1 | 3/2006 | Smith | |
| 2006/0065833 A1 | 3/2006 | Craig et al. | |
| 2006/0118712 A1 | 6/2006 | Yang et al. | |
| 2007/0045541 A1 | 3/2007 | Urey et al. | |
| 2007/0114431 A1 | 5/2007 | Wang et al. | |
| 2008/0048126 A1 | 2/2008 | Janssen et al. | |
| 2008/0224031 A1 | 9/2008 | Gilchrist | |
| 2008/0265150 A1 | 10/2008 | Holmes | |

OTHER PUBLICATIONS

PCT International Search Report; International App. No. PCT/US2006/048136; Nov. 7, 2008; pp. 1-2.

PCT International Search Report; International App. No. PCT/US 07/04209, Nov. 26, 2008, pp. 1-2.

Bergman, David J.; Stockman, Mark I.; "Surface Plasmon Amplification by Stimulated Emission of Radiation: Quantum Generation of Coherent Surface Plasmons in Nanosystems"; Physical Review Letters; bearing dates of Sep. 15, 2002, Jan. 14, 2003, Jan. 17, 2003, and 2003; pp. 027402-1-027402-4; vol. 90, No. 2; The American Physical Society.

Brock, Jeffrey B.; Houck, Andrew A.; Chuang, Isaac L.; "Focusing inside negative index materials"; Applied Physics Letters; bearing dates of Apr. 19, 2004, Jul. 28, 2004, Sep. 27, 2004, Nov. 8, 2004, and 2004; pp. 2472-2474; vol. 85, No. 13; American Institute of Physics.

Caloz, Christophe; Itoh, Tatsuo; *Electromagnetic Metamaterials: Transmission Line Theory and Microwave Applications*; bearing a date of Nov. 2005; ISBN: 0-471-75431-5; Wiley-IEEE Press.

Dalton, Larry R.; "Integrated Optics/Electronics Using Electro-Optic Polymers"; Mat. Res. Soc. Symp. Proc.; bearing a date of 2004; pp. L.7.2.1-L.7.2.12; vol. 817; Materials Research Society.

Driessen, Alfred; Dekker, Ronald; Diemeer, Mart B.J.; Geuzebroek, Douwe H.; Hoekstra, Hugo J.W.M.; Klein, Edwin J.; and Leinse, Arne; "Microresonators as promising building blocks for VLSI photonics"; Proceedings of SPIE—Integrated Optics: Theory and Applications; bearing dates of Aug. 31-Sep. 2, 2005; pp. 59560Q1-59560Q14 + Cover Pg and Blank Pg (16 pages total); vol. 5956; The International Society for Optical Engineering.

Eleftheriades, G. V.; Balmain, K. G; *Negative Refraction Metamaterials: Fundamental Principles and Applications*; bearing a date of Jul. 7, 2005; ISBN: 0-471-60146-2; Wiley-IEEE Press.

Fang, Nicholas; Zhang, Xiang; "Imaging properties of a metamaterial superlens"; Applied Physics Letters; bearing dates of Sep. 24, 2002, Nov. 18, 2002, Jan. 13, 2003 and 2003; pp. 161-163; vol. 82, No. 2; American Institute of Physics.

Gay-Balmaz, Philippe; Martin, Olivier J.F.; Electromagnetic resonances in individual and coupled split-ring resonators; Journal of Applied Physics; bearing dates of Dec. 27, 2001, Jun. 10, 2002, Sep. 1, 2002, and 2002; pp. 2929-2936; vol. 92, No. 5; American Institute of Physics.

Gonzalez, Francisco Javier; Alda, Javier; LLIC, Bojan; Boreman, Glenn D.; "Infrared antennas coupled to lithographic Fresnel zone plate lenses"; Applied Optics; bearing dates of May 3, 2004, Aug. 17, 2004, Aug. 20, 2004, Nov. 20, 2004 and 2004; pp. 6067-6073; vol. 43, No. 33; Optical Society of America.

Greegor, R.B., Parazzoli, C.G., Nielsen, J.A., Thompson, M.A., Tanielian, M.H., and Smith, D.R.; "Simulation and testing of a graded negative index of refraction lens"; Applied Physics Letters; bearing dates of Jan. 26, 2005, Jul. 11, 2005, Aug. 25, 2005 and 2005; pp. 091114-1-091114-3; vol. 87, Issue 091114; American Institute of Physics; located at: http://ceta.mit.edu/adm/LHM_paper/papers/257.pdf; printed on Dec. 19, 2005.

Jenkins, Francis A.; White, Harvey E.; *Fundamentals of Optics—Fourth Edition*; bearing dates of 1937, 1950, 1957, and 1976; ISBN: 0-07-032330-5; McGraw-Hill, Inc.

Jimenez, J.L.; Fonseca, L.R.C.; Brady, D.J.; Leburton, J.P.; Wohlert, D.E.; Cheng, K.Y.; "The quantum dot spectrometer"; Appl. Phys. Lett.; bearing dates of Dec. 15, 1997, Jun. 7, 2002, Oct. 14, 1997, Sep. 15, 1997, and 1997; pp. 3558-3560; vol. 71, No. 24; American Institute of Physics.

Li, Le-Wei; Yao, Hai-Ying; Wu, Qun; and Chen, Zhi-Ning; "Broad-bandwidth and low-loss metamaterials: theory, design and realization," Journal of Zhejiang University Science A; bearing dates of Sep. 5, 2005, Oct. 10, 2005, and 2006; printed on Feb. 15, 2006; pp. 5-23; vol. 7; Issue 1; located at: http://www.edu.cn/jzus/2006/A0601/A060102.pdf.

Pedrotti, S.J., Frank L.; Pedrotti, Leno S.; *Introduction to Optics—Second Edition*; bearing dates of 1993, 1987; ISBN: 0-13-501545-6; Prentice-Hall, Inc.

Pendry, J.B.; "Negative Refraction Makes a Perfect Lens"; Physical Review Letters; bearing dates of Apr. 25, 2000, Oct. 30, 2000 and 2000; pp. 3966-3969; vol. 85, No. 18; The American Physical Society.

Shelby, R.A.; Smith, D.R.; Schultz, S.; "Experimental Verification of a Negative Index of Refraction"; Science; bearing dates of Jan. 8, 2001, Feb. 22, 2001, and Apr. 6, 2001; pp. 77-79; vol. 292; located at: www.sciencemag.org.

Smith, D.R., Mock, J.J., Starr, A.F., Schurig, D.,; "A gradient index metamaterial"(Pre-Print); bearing dates of Jul. 7, 2004 and Jul. 11, 2004; pp. 1-5; located at: http://arxiv.org/ftp/physics/papers/0407/0407063.pdf; printed on Dec. 19, 2005.

Smith, D.R.; Padilla, Willie J.; Vier, D.C.; Nemat-Nasser, S.C.; Schultz, S.; "Composite Medium with Simultaneously Negative Permeability and Permittivity"; Physical Review Letters; bearing dates of Dec. 2, 1999, May 1, 2000, and 2000; pp. 4184-4187; vol. 84, No. 18; The American Physical Society.

Smith, D.R.; Pendry, J.B.; Wiltshire, M.C.K.; "Metamaterials and Negative Refractive Index"; Science-Review; bearing a date of Aug. 6, 2004; pp. 788-792; vol. 305; located at: www.sciencemag.org.

Smith, David R.; Rye, Patrick; Vier, David C.; Starr, Anthony F.; Mock, Jack J.; and Perram, Timothy; "Design and Measurement of Anisotropic Metamaterials that Exhibit Negative Refraction"; IEICE Trans. Electron; bearing dates of Sep. 3, 2003, Nov. 25, 2003, and Mar. 2004; pp. 359-370; vol. E87-C, No. 3.

Smith, David R.; Vier, David C.; "Design of Metamaterials with Negative Refractive Index"; Proc. of SPIE; pp. 52-63; vol. 5359.

Soukoulis, Costas M.; Photonic Crystals and Light Localization in the 21st Century; Proceedings of the NATO Advanced Study Institute on Photonic Crystals and Light Localization, Crete, Greece, Jun. 18-30, 2000 (NATO Science Series: C: Mathematical & Physical Sciences); bearing dates of Jun. 18-30, 2000 and May 1, 2001; ISBN: 0-792-36948-3; NATO Science Series: C: Mathematical & Physical Sciences; Kluwer Academic Publishers.

Wang, Y.; Kempa, K.; Kimball, B.; Carlson, J.B.; Benham, G.; Li, W.Z.; Kempa, T.; Rybczynski, J.; Herczynski, A.; Ren, Z.F.; "Receiving and transmitting light-like radio waves: Antenna effect in arrays of aligned carbon nanotubes"; Applied Physics Letters; bearing dates of Jun. 4, 2004, Jul. 26, 2004, Sep. 27, 2004, Sep. 29, 2004, and 2004; pp. 2607-2609; vol. 85, No. 13; American Institute of Physics.

Xu, W.; Li, L.-W.; Yao, H.-Y.; Yeo, T.-S. Wu, Q.; "Extraction of Constitutive Relation Tensor Parameters of SRR Structures Using Transmission Line Theory"; J. of Electromagn. Waves and Appl.; bearing a date of 2006; pp. 13-25; vol. 20, No. 01.

Yang, Suxia; Page, J.H.; Liu, Zhengyou; Cowan, M.L.; Chan, C.T.; Sheng, Ping; "Focusing of Sound in a 3D Phononic Crystal"; Physical Review Letters; bearing dates of Mar. 1, 2004, Jul. 7, 2004, Jul. 9, 2004, and 2004; pp. 024301-1-024301-4; vol. 93, No. 2; The American Physical Society.

VARIABLE MULTI-STAGE WAVEFORM DETECTOR

CROSS-REFERENCE TO RELATED APPLICATIONS

For purposes of the USPTO extra-statutory requirements, the present application constitutes a continuation-in-part of U.S. patent application Ser. No. 11/588,851, titled VARIABLE MULTI-STAGE WAVEFORM DETECTOR, naming Roderick A. Hyde, Muriel Y. Ishikawa, Edward K. Y. Jung, Nathan P. Myhrvold, Clarence T. Tegreene, and Lowell L. Wood, Jr. as inventors, filed on Oct. 26, 2006 now U.S. Pat. No. 7,427,762, which is entitled to the benefit of the filing date.

For purposes of the USPTO extra-statutory requirements, the present application constitutes a continuation-in-part of U.S. patent application Ser. No. 12/077,441, entitled MULTI-STAGE WAVEFORM DETECTOR, naming Roderick A. Hyde, Muriel Y. Ishikawa, Edward K. Y. Jung, Nathan P. Myhrvold, Clarence T. Tegreene, and Lowell L. Wood, Jr. as inventors, filed 18 Mar. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/079,735, entitled MULTI-STAGE WAVEFORM DETECTOR, naming Roderick A. Hyde, Muriel Y. Ishikawa, Edward K. Y. Jung, Nathan P. Myhrvold, Clarence T. Tegreene, and Lowell L. Wood, Jr. as inventors, filed 28 Mar. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/215,064, entitled MULTI-STAGE WAVEFORM DETECTOR, naming Roderick A. Hyde, Muriel Y. Ishikawa, Edward K. Y. Jung, Nathan P. Myhrvold, Clarence T. Tegreene, and Lowell L. Wood, Jr. as inventors, filed 24 Jun. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/215,155, entitled MULTI-STAGE WAVEFORM DETECTOR, naming Roderick A. Hyde, Muriel Y. Ishikawa, Edward K. Y. Jung, Nathan P. Myhrvold, Clarence T. Tegreene, and Lowell L. Wood, Jr. as inventors, filed 24 Jun. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/218,226, entitled VARIABLE MULTI-STAGE WAVEFORM DETECTOR, naming Roderick A. Hyde, Muriel Y. Ishikawa, Edward K. Y. Jung, Nathan P. Myhrvold, Clarence T. Tegreene, and Lowell L. Wood, Jr. as inventors, filed 10 Jul. 2008, which is currently co-pending, or is an application of which a currently co-pending application is entitled to the benefit of the filing date.

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/314,978, entitled MULTI-STAGE WAVEFORM DETECTOR, naming Roderick A. Hyde, Muriel Y. Ishikawa, Edward K. Y. Jung, Nathan P. Myhrvold, Clarence T. Tegreene, and Lowell L. Wood, Jr. as inventors, filed 21 Dec. 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/355,493, entitled VARIABLE METAMATERIAL APPARATUS, naming Roderick A. Hyde; Nathan P. Myhrvold; Clarence T. Tegreene; and Lowell L. Wood, Jr. as inventors, filed 16 Feb. 2006, which is currently co-pending, or is an application of which a currently co-pending application is entitled to the benefit of the filing date. The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

An embodiment provides a variable system for interacting with electromagnetic or other energy that includes a first detector assembly arranged relative to a second detector assembly.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1:
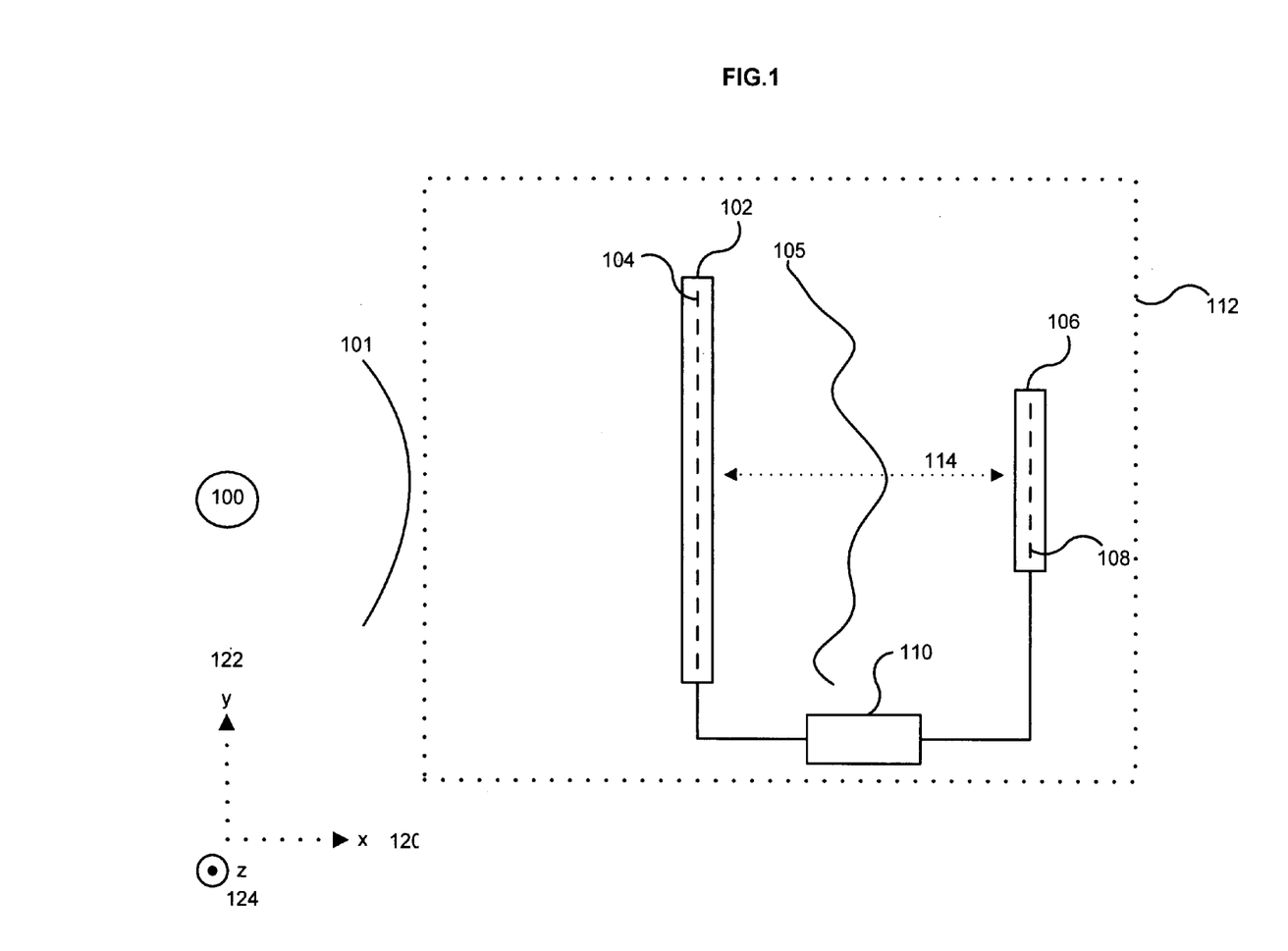
FIG. 1 shows a first embodiment of a detector system.

In a first embodiment, shown in FIG. 1, a source 100 provides a first wave 101 to a detector system 112, where the detector system 112 includes an array of subassemblies or detectors 104, arranged to form a first detector assembly 102. The wave 101 may be any kind of wave, including (but not limited to) an electromagnetic, acoustic, mechanical, or particle wave. The detectors 104 may include (but are not limited to) quantum dots, antennae, photo-detectors, resonant structures, or any number of devices or structures that can detect or interact with energy. The size, type, number, orientation, separation, homogeneity, and other features of the detectors 104 may be dependent on the wavelength of the energy that the array is configured to detect, the size of the source 100, the distance between the source 100 and the first detector assembly 102, relative orientations, positions, or other relative aspects of the source 100 and first detector assembly 102, polarization of the wave 101, or a variety of other design considerations.

As a portion of the energy in the wave 101 interacts with the first detector assembly 102, a second portion of the energy in the wave 101 may travel past the first detector assembly 102, and energy may be re-emitted from the first detector assembly 102, as well. The second portion and the re-emitted energy combine in whole or in part to form a second wave 105 that travels as indicated in FIG. 1. A second array of detectors 108 that forms a second detector assembly 106 is positioned to intercept the second wave 105. The detectors 108 in the second detector assembly 106 may be any of the kinds of detectors 104 that were described for the first detector assembly 102. While the detectors 108 may be substantially identical in type to the detectors 104, they may also differ in type, size, density or other aspects from the detectors 104.

The number, arrangement, orientation and other aspects of the detectors 104, 108 may vary according to design considerations. The assemblies 102, 106 may or may not include a substrate, the substrate being contiguous or having spacings. In one approach, each detector assembly 102, 106 may comprise a single detector having characteristics such as position, size, shape and orientation selected according to the particular design. Alternatively, one or more of the detector assemblies 102, 106 may be configured with a plurality of detectors 104, 108 having a density such that the detectors 104, 108 may interact with respective portions of the waves 101, 105. While the illustrative arrangements of the detectors 104, 108 are presented with relatively simple arrangements and with a relatively small number of individual detectors 104, 108 for clarity of presentation, the detector assemblies 102, 106 may include more or fewer detectors 104, 108 and may be arranged in a variety of configurations depending on the particular design of the detector system 112. Further, although the illustrative example includes two assemblies 102, 106, the principles and structures herein can be adapted for detector systems 112 that include three or more detector assemblies 102, 106.

Responsive to the first wave 101 and the second wave 105, the detectors 104, 108 produce respective signals corresponding to the first and second waves 101, 105. In one approach, the respective signals travel to a signal processor 110. While the embodiment shows a single signal processor 110 that receives signals from detectors 104 and 108, in other configurations each of the signals may travel to a respective processor 110 or to more than one processor 110. Moreover, although the signal processor 110 is shown as separate from the detectors 104, 108, the signal processor 110 and one or more of the detectors 104, 108 may be part of a single assembly. In still another approach, other components, such as amplifiers, filters, wireless couplers, mixers, or other components may be interposed between the detectors 104, 108 and the signal processor 110 or may be integral to the signal processor 110. Further, in some applications, the signals from the detectors 104, 108 may be used directly or supplied to an external system without significant processing.

Although FIG. 1 is shown with the source 100 providing the first wave 101 directly to the first detector assembly 102, in another embodiment the first wave 101 may not travel directly from the source 100 to the first detector assembly 102. For example, the first wave 101 may encounter a lens, diffractive element, obstruction, hologram, object to be imaged, or a different object between the source 100 and the first detector assembly 102.

The source 100 may, for example, be a laser, an acoustic transducer, a natural source of waves such as solar energy, or a different source of waves. The source 100 may be configured to produce coherent or incoherent radiation and may be configured to scan over an energy range or to spatially scan over the detector system 112. Further, although the embodiment in FIG. 1 is shown with a single source 100, more than one source may produce the wave 101, or the source of the wave 101 may be unknown. The wave 101, although shown having a simple curved wavefront in FIG. 1, may be any shape or form.

Figure 2:
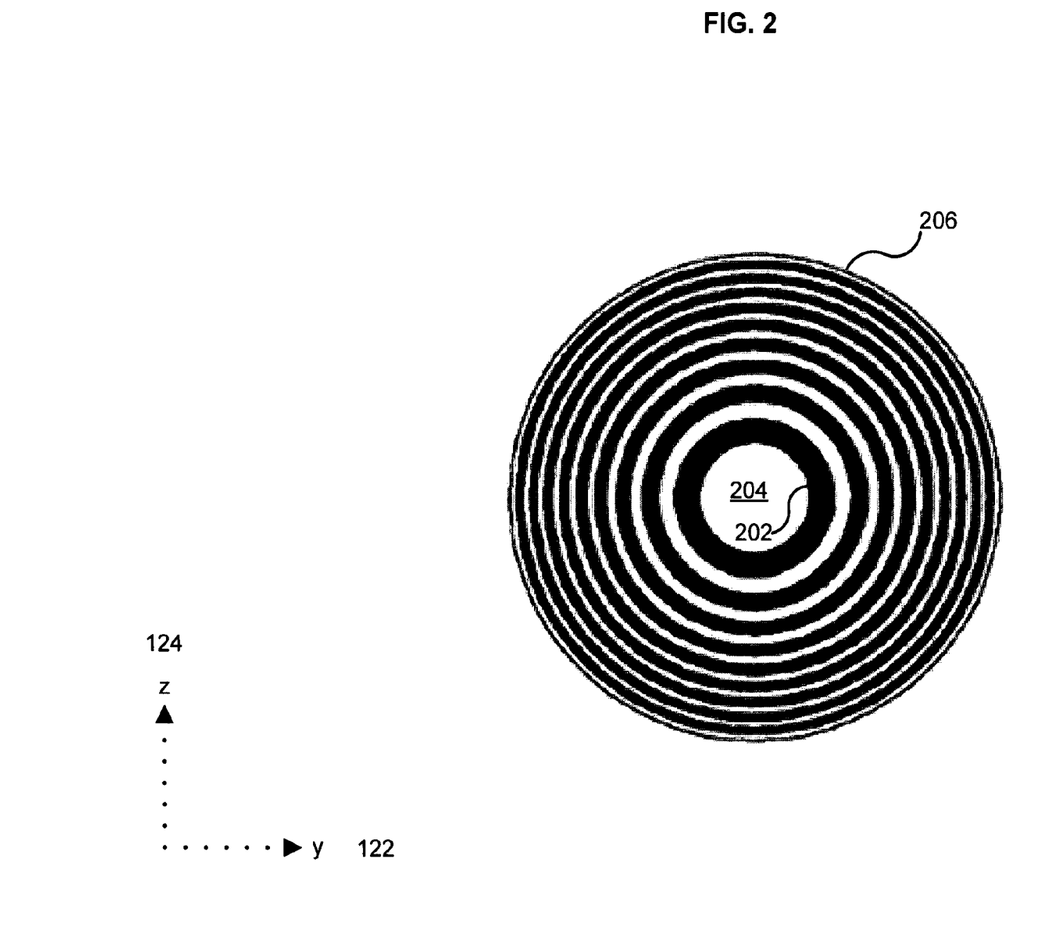
FIG. 2 shows a zone plate.

In one embodiment, the detectors 104 may be arranged to form the zone plate 206 shown in FIG. 2. In this case the detectors 104 may be arranged in alternating sections 202, 204 that are substantially concentric as shown in FIG. 2. The zone plate 206 may be included in the first detector assembly 102, and the second detector assembly 106 may be positioned at the focal plane of the zone plate 206 or at a different location relative to the zone plate 206. The focusing of the arrangement may be dependent on the density of the detectors 104, and in some arrangements, other material may be included in the detector assembly 102 to further define the sections 202, 204. Zone plates are described in F. A. Jenkins and H. E. White, "FUNDAMENTALS OF OPTICS", Fourth Edition, McGraw-Hill, 1976, which is incorporated herein by reference.

In one case the alternating sections 202, 204 may be substantially opaque and transparent, respectively, where the detectors 104 are effectively opaque to the energy incident on them and are positioned to form the sections 202. Examples of such detectors 104 may include, but are not limited to, parabolic reflector antennae or photo-detectors. Although the sections 202, 204 are described in this embodiment as being opaque or transparent, it may be the case that not every section 202 is opaque and not every section 204 is transparent, or the opaque sections 202 may not be entirely opaque and the transparent sections 204 may not be entirely transparent. One skilled in the art may recognize that an element having the desired features may still be achieved even if the design of the zone plate 206 differs from that described in Jenkins and White.

In another case the alternating sections 202, 204 may be phase-shifting and transparent, respectively, where the detectors 104 may be resonant structures such that they absorb and re-resonate energy and are positioned to form the sections 202. Examples of such structures may include some antennae, split ring resonators, quantum dots, or a different kind of detector. Although the sections 202, 204 are described in this embodiment as being phase-shifting or transparent, it may be the case that not every section 202 is phase-shifting and not every section 204 is transparent, or the phase-shifting sections 202 may not be entirely phase-shifting and the transparent sections 204 may not be entirely transparent. Moreover, some of the sections 202, 204 may be partially transmissive or have some gradation of phase, absorption or gain.

Although the zone plate 206 in FIG. 2 is shown having circular sections 202, 204 it is not necessary for a zone plate 206 to have circular sections. For example, a square zone plate is described in F. J. González, J. Alda, B. Ilic, and G. D. Boreman, "INFRARED ANTENNAS COUPLED TO LITHOGRAPHIC FRESNEL ZONE PLATE LENSES", Applied Optics, Volume 43, Number 33, Nov. 20, 2004, which is incorporated herein by reference, and other geometries may also be implemented as appropriate.

The detectors 104 may be arranged to change the phase of the first wave 101 in a spatially varying manner to focus the wave, form an image, or for another purpose. For example, the detectors 104 may be arranged analogously to a Gabor zone plate or a hologram as described in F. L. Pedrotti and L. S. Pedrotti, "INTRODUCTION TO OPTICS", Second Edition, Prentice-Hall, Inc., 1993, which is incorporated herein by reference. The phase of the wave 101 may be varied by varying the density of detectors 104, by varying the properties of the detectors 104, or in some other way.

Figure 3:
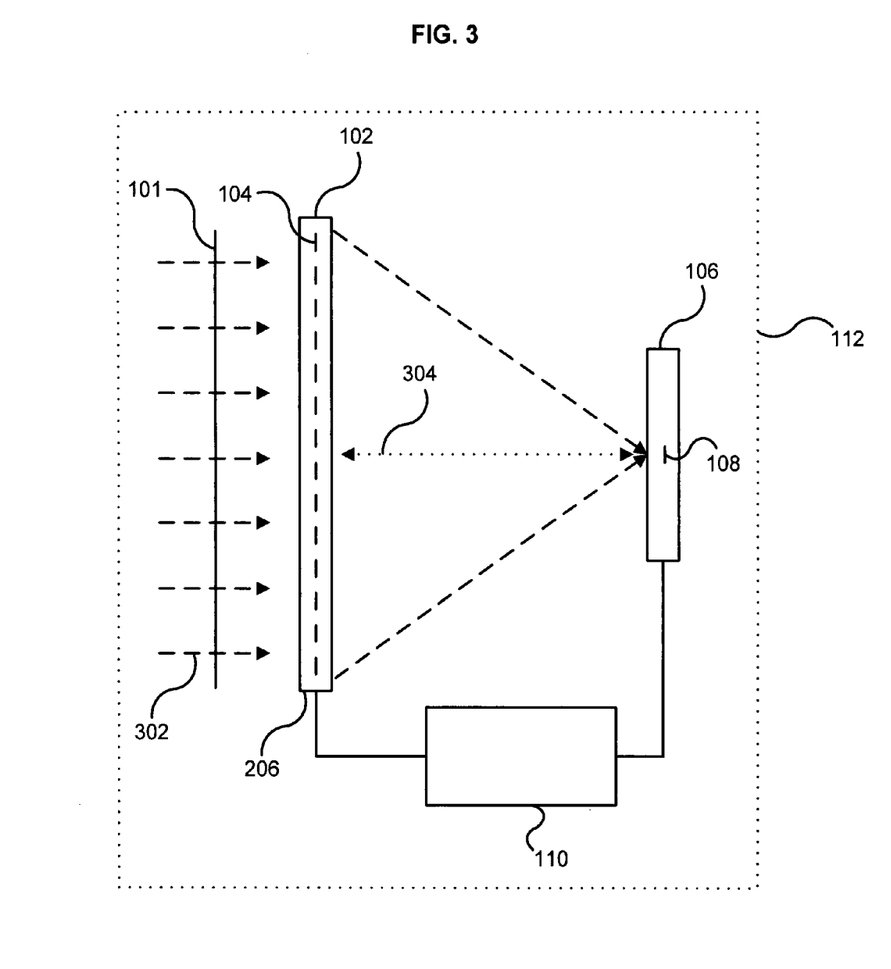
FIG. 3 shows an embodiment of the detector system.

FIG. 3 shows the detector system 112 where the first detector assembly 102 is arranged to form a focusing element, where the focusing element may be a zone plate 206. Parallel incoming rays 302 are incident on the first detector assembly 102 and are focused to the second detector assembly 106, where in this embodiment the second detector assembly 106 includes a single detector 108. Information from the detectors 104, 108 is transmitted to the signal processor 110. FIG. 3 is shown with a single detector 108 located a focal distance 304 away from the zone plate 206, however the second detector assembly 106 may comprise more than one detector 108, and the detector may not be at the focal point of the zone plate 206. Further, FIG. 3 is shown with parallel incoming rays 302 (where the rays 302 show the direction of propagation of the wave 101) incoming at normal incidence to the first detector assembly 102, however the wave 101 need not impinge on the first detector assembly 102 at normal incidence as shown in FIG. 3 and the wave 101 need not be a substantially plane wave.

Figure 4:
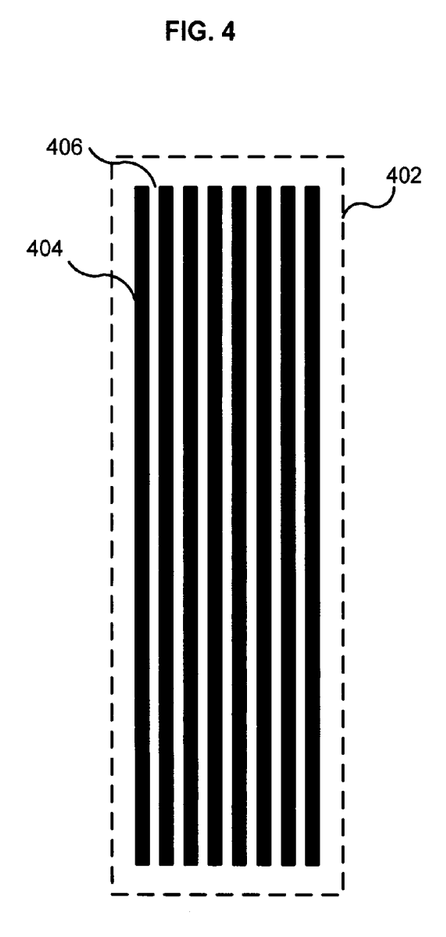
FIG. 4 shows a diffraction grating.

In another embodiment, the detectors 104 may be arranged as a diffraction grating 402 having alternating sections 404, 406 that are substantially parallel, as shown in FIG. 4. The diffraction grating 402 may be included in the first detector assembly 102, and the second detector assembly 106 may be positioned to receive radiation diffracted by the grating 402. The properties of the grating 402 may be dependent on the width of the sections 404, 406, the number of sections 404, 406, or another parameter. Diffraction gratings are described in Jenkins and White.

In one approach the alternating sections 404, 406 may be substantially opaque and transparent, respectively, where the detectors 104 are effectively opaque to the energy incident on them and are positioned to form the sections 404. In another case the alternating sections 404, 406 may be phase-shifting and transparent, respectively, where the detectors 104 may be resonant structures such that they absorb and re-resonate energy and are positioned to form the sections 404. In another case, sections 404 and 406 may both include phase-shifting detectors such that the detectors 104 in sections 404 and the detectors 104 in sections 406 phase shift by different amounts to form a diffraction grating 402. In some arrangements, other material may be included in the diffraction grating 402 to further define the sections 404, 406. As described for the zone plate 206, one skilled in the art may recognize that a selected optical or other response features may still be produced even if the design of the diffraction grating 402 described in Jenkins and White is not adhered to exactly.

Figure 5:
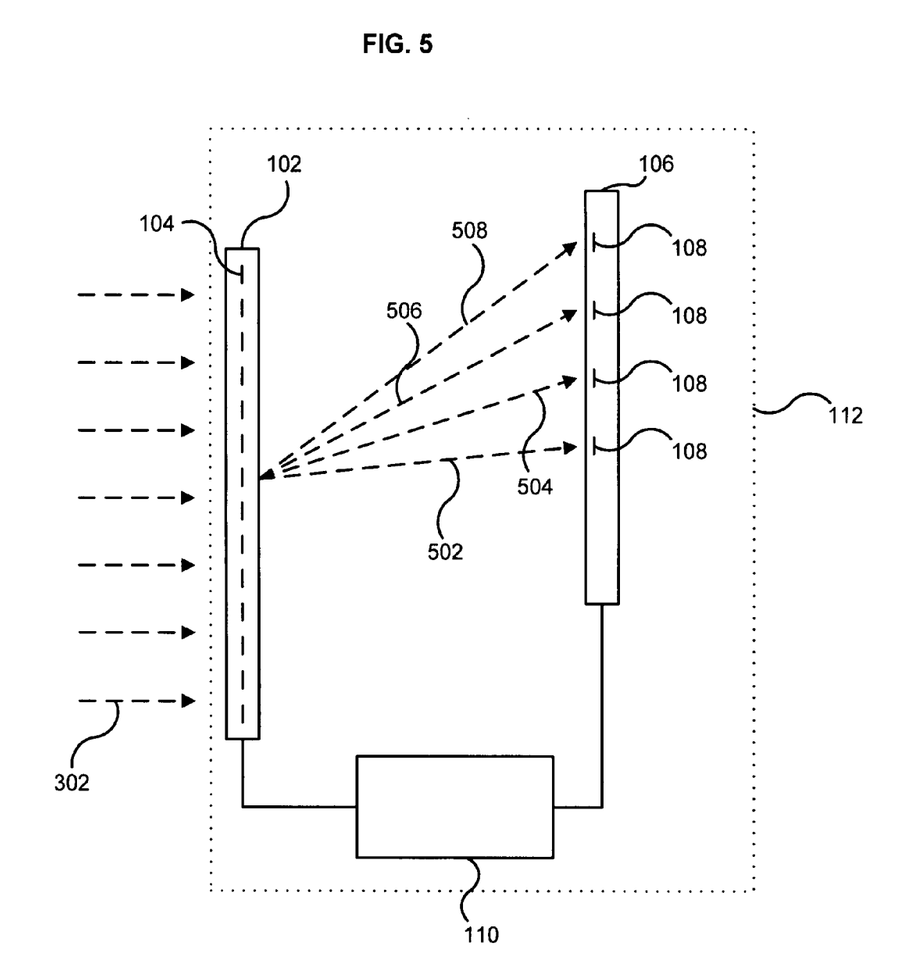
FIG. 5 shows an embodiment of the detector system.

FIG. 5 shows the detector system 112 where the detectors 104 in the first detector assembly 102 are arranged to form a diffraction grating 402. Parallel incoming rays 302 are incident on the first detector assembly 102 and are diffracted to the second detector assembly 106, where the second detector assembly 106 may be positioned to receive radiation diffracted by the grating 402. The diffraction grating 402 is configured to diffract different frequencies of radiation (represented by rays 502, 504, 506, 508) at different angles, and the second detector assembly 106 may be positioned with one or more detectors 108 positioned to receive energy of a given frequency or range of frequencies. Information from the detectors 104, 108 is transmitted to the signal processor 110. FIG. 5 is shown with four detectors 108 approximately equally spaced, however the second detector assembly 106 may comprise any number of detectors 108, and the detectors 108 may be located at any place on the second detector assembly 106. Further, FIG. 5 is shown with parallel incoming rays 302 (where the rays 302 show the direction of propagation of the wave 101) incoming at normal incidence to the first detector assembly 102, however the wave 101 need not impinge on the first detector assembly 102 at normal incidence as shown in FIG. 5 and the wave 101 need not be a substantially plane wave.

FIG. 5 shows both detector assemblies 102, 106 connected to the signal processor 110, however in some configurations it is not necessary for the detector assemblies 102, 106 to be connected to the signal processor 110. Or, only one of the detector assemblies 102 or 106 may be connected to the signal processor 110.

The configuration in FIG. 5 may be such that the detector assembly 102 is arranged to detect radiation in a range of energies and incoming angles and the detector assembly 106 is configured to detect radiation in a different range of energies and incoming angles, as described for the configuration in FIG. 3. The detector(s) 108 may be positioned, as shown in FIG. 5, such that each detector 108 receives a different energy band.

Although the embodiments in FIGS. 1, 3, and 5 are described as having two detector assemblies 102, 106, the detector system 112 may include more than two detector assemblies. In such arrangements, either or both of the detector assemblies may provide, shape or otherwise influence the first and/or second waves to produce additional waves for interaction with a third detector assembly (not shown). Similarly, as additional detector assemblies are included, each may act as both a detector assembly and as a structure that interacts with energy. Moreover, portions of energy can propagate from the additional detector assemblies in a similar fashion to the second wave.

Further, FIGS. 1, 3, and 5 show the first and second detector assemblies 102, 106 being centered about (or substantially centered about) a common location along the y direction 122. However, in some embodiments it may be desirable for the detector assemblies 102, 106 to be offset from each other along the y direction 122. Although the detector assemblies 102, 106 are shown as being substantially planar, it is not necessary for them to be planar and they may take any shape.

The signals from the detectors 104, 108 may be delivered to the signal processor 110 in a variety of ways. For detectors 104, 108 that generate an electrical signal, such as many kinds of antennae, photodetectors, or acoustic transducers, the signals from the detectors 104, 108 may be delivered to the signal processor 110 electrically. For detectors 104, 108 that receive electromagnetic energy, the signals from the detectors 104, 108 may be delivered to the signal processor 110 via a waveguide such as an optical fiber, via free space or in a different way. Although electrical and electromagnetic signals are presented as examples of forms that the signal may take, one skilled in the art will recognize that the type of signal may depend on the type of detector, and may adjust the signal processor 110 based on the type or types of signals input to the signal processor 110. The signals from all of the detectors 104, 108 may all be of the same form, for example all electrical signals or all electromagnetic signals, or different signals from the detectors 104, 108 may be delivered to the signal processor 110 in different forms.

Although the above embodiments are described in terms of having only one kind of detector, it may be desirable in some configurations to include more than one kind of detector. For example, the first or second detector assembly 102, 106 may include antennae of different sizes, or they may include both antennae and photodetectors. These configurations are illustrative examples of the different combinations of detectors 104, 108 that may be configured, and many other configurations are possible.

Returning to the illustrative embodiments of FIGS. 1, 3, and 5, the first wave 101 is described as impinging on the first detector assembly 102 for simplicity of explanation. The first wave 101 is representative of energy incident on the first detector assembly 102 and is not limited to monochromatic plane waves, and can include any kind of energy distribution, including those with a range of energies, irregular wavefronts, or distributions where the spatial and frequency range of the energy is unknown.

The detectors 104, 108 are configured to receive energy having an energy distribution, the energy distribution including a frequency range. This frequency range may be very small such that the detectors 104, 108 are considered to detect substantially one frequency, or the frequency response of the detectors 104, 108 may be a function of frequency. The detectors 104, 108 may all detect energy in substantially the same frequency range, or the detectors 104 in the first detector assembly 102 may detect energy in a first frequency range and the detectors 108 in the second detector assembly 106 may detect energy in a second frequency range, or the detector assemblies 102, 106 may include a variety of detectors 104, 108 that receive energy in a variety of frequency ranges.

In one embodiment, one or both of the detector assemblies 102, 106 may include a device that receives energy and may guide the energy to detectors 104, 108, such as a concentrator designed to receive solar energy as described, for example, in U.S. Pat. No. 4,149,902 entitled FLUORESCENT SOLAR ENERGY CONCENTRATOR to Mauer, et al., which is incorporated herein by reference. In one embodiment, the concentrator may be formed in the shape of the zone plate 206 shown in FIG. 2, such that the first detector assembly 102 includes the zone plate 206 and the detectors 104 are configured to receive the energy from the concentrator, where the zone plate 206 is incorporated into the detector system 112 as described in FIG. 3. Although the embodiment is described with the concentrator shaped as a zone plate 206 configured to be included in the first detector assembly 102, the concentrator may have a different shape, and may be included in the second detector assembly 106 or both the first and second detector assemblies 102, 106, where detectors 104, 108 may be positioned to receive the energy collected. The device may be a solid planar device or may be shaped to focus or direct energy. Further, although a device that receives and guides solar energy is described, one skilled in the art may extend the concept to different frequency ranges or different kinds of energy.

In one embodiment the first or second detector assemblies 102, 106 may include a metamaterial. Examples of metamaterials can be found in R. A. Shelby, D. R. Smith, and S. Schultz, "EXPERIMENTAL VERIFICATION OF A NEGATIVE INDEX OF REFRACTION", Science, Volume 292, Apr. 6, 2001; D. R. Smith, W. J. Padilla, D. C. Vier, S. C. Nemat-Nasser, and S. Schultz, "COMPOSITE MEDIUM WITH SIMULTANEOUSLY NEGATIVE PERMEABILITY AND PERMITTIVITY", Physical Review Letters, Volume 84, Number 18, May 1, 2000; D. R. Smith, J. B. Pendry, M. C. K. Wiltshire, "METAMATERIALS AND NEGATIVE REFRACTIVE INDEX", Science, Volume 305, Aug. 6, 2004; D. R. Smith and D. C. Vier, "DESIGN OF METAMATERIALS WITH NEGATIVE REFRACTIVE INDEX", Proceedings of SPIE, Volume 5359, Quantum Sensing and Nanophotonic Devices, Manijeh Razeghi, Gail J. Brown, Editors, July 2004, pp. 52-63; each of which is incorporated herein by reference. Although the above references describe metamaterials having negative index of refraction, other metamaterials have effective refractive indices that are positive, negative or some combination thereof.

One example of a metamaterial, described in D. R. Smith, W. J. Padilla, D. C. Vier, S. C. Nemat-Nasser, and S. Schultz, "COMPOSITE MEDIUM WITH SIMULTANEOUSLY NEGATIVE PERMEABILITY AND PERMITTIVITY", Physical Review Letters, Volume 84, Number 18, May 1, 2000, includes an array of split ring resonators and wires. In this case, the array may be configured to form the first detector assembly 102, where the individual split ring resonators and wires form the detectors 104. In one embodiment, the metamaterial may be arranged to have a gradient index of refraction as described in D. R. Smith, J. J. Mock, A. F. Starr, and D. Schurig, "A GRADIENT INDEX METAMATERIAL", available at: http://arxiv.org/abs/physics/0407063; and R. B. Greegor, C. G. Parazzoli, J. A. Nielsen, M. A. Thompson, M. H. Tanielian, and D. R. Smith, "SIMULATION AND TESTING OF A GRADED NEGATIVE INDEX OF REFRACTION LENS," Applied Physics Letters, Volume 87, page 091114, Aug. 29, 2005, each of which is incorporated herein by reference.

Figure 6:
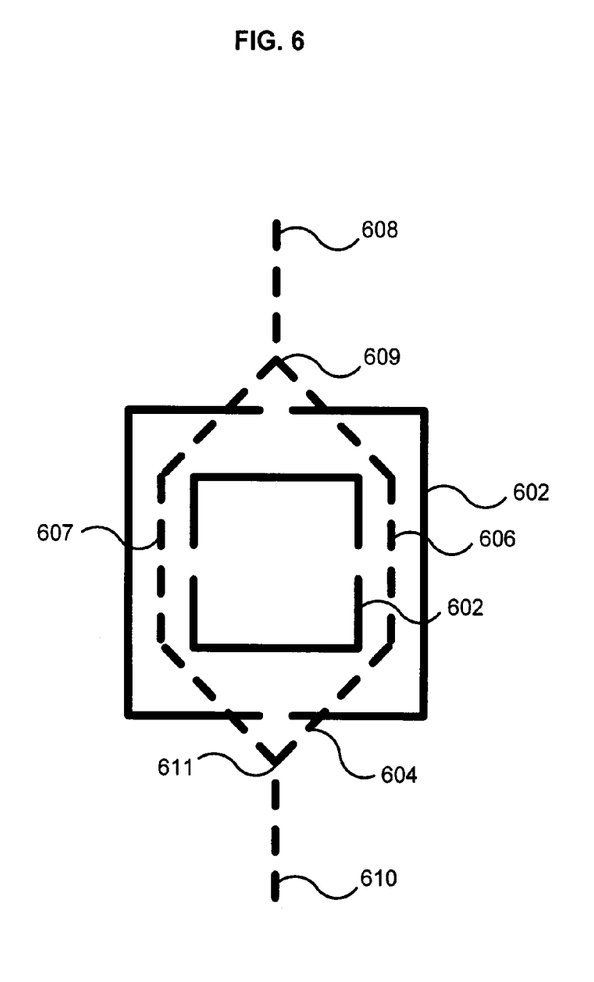
FIG. 6 shows a split ring resonator and an interferometer.

The embodiment in FIG. 6 demonstrates one way of extracting a signal from an array including a split ring resonator. FIG. 6 shows a split ring resonator 602 proximate to an optical interferometer 604, where the interferometer 604 includes an electrooptic polymer. The interferometer 604 is similar to a Mach-Zehnder interferometer, described in Jenkins and White. The interferometer 604 is configured with an input end 608, an output end 610, and two straight sections 606, 607. One or both of the straight sections 606, 607 includes or is substantially adjacent to a region having an electrooptic polymer. The interferometer 604 is configured to receive electromagnetic energy, such as light energy, at the input end 608, and guide the electromagnetic energy. The electromagnetic energy divides, typically into two substantially equal portions at the first branch 609. A first portion travels through one of the straight sections 606 and the other through the other straight section 607.

The energy from the straight sections 606, 607 recombines at the second branch 611, and provides an output signal at the output end 610. When the split ring resonator 602 responds to incoming electromagnetic energy, the resonator produces localized fields, due to induced currents and/or electrical potentials in the resonator 602. The localized fields interact with the electrooptic polymer and produce variations in the effective refractive index experienced by the guided energy. This then changes the effective path length of the arm(s) 606, 607 of the interferometer 604 that include the electrooptic polymer. As is known for interferometric modulators and switches, the amount of light exiting the output end is a function of the relative change in effective refractive index in the legs of the interferometer, thus providing information about the current in the split ring resonator 602. One straight section 606 or 607 of the interferometer 604 may partially or entirely comprise an electrooptic polymer, both straight sections 606, 607 may comprise electrooptic polymer, or the entire interferometer 604 may comprise electrooptic polymer. The interferometer 604 may include waveguiding portions that are defects etched in a material, portions including waveguiding dielectric, portions that allow electromagnetic energy to propagate in free space, or other configurations. Moreover, the position of the interferometer 604 relative to the split ring resonator 602 is one illustrative example and the relative positions may be different from that shown in FIG. 6 and may still provide a signal responsive to current in the split ring resonator 602. Further, although the split ring resonator 602 in FIG. 6 is shown having substantially rectilinear geometry, this is not required and other split ring resonator geometries are known to those skilled in the art. Further, although the illustrative embodiment presents one interferometric approach, other approaches to detecting electromagnetic energy in the resonators may use interferometric or non-interferometric approaches. For example, L. Dalton, "Integrated Optics/Electronics Using Electro-Optic Polymers", Mat. Res. Soc. Symp. Proc., 2004, Volume 817, Pages L7.2.1-L7.2.12, shows one approach to detecting fields using electrooptic polymers. Similarly, structures can utilize frequency shifting induced by fields, such as is described in A. Driessen et al., "Microresonators as promising building blocks for VLSI photonics", Proceedings of SPIE, Integrated Optics: Theory and Applications, 2005, Volume 5956, Pages 59560Q-1-59560Q-14.

Another way of extracting signals from a metamaterial array is by including one or more antennae in the array. Measurements of the fields inside a metamaterial comprising split ring resonators and wires using a scannable antenna are described in J. B. Brock, A. A. Houck, and I. L. Chuang, "FOCUSING INSIDE NEGATIVE INDEX MATERIALS", Applied Physics Letters, Volume 85, Number 13, Sep. 27, 2004, which is incorporated herein by reference. Although an antenna is one way of extracting the signal from the metamaterial, the signals may be extracted in other approaches. For example, the signal may be sampled using one or more switched circuits coupled to the resonators. In still another example, the signal may be measured by directly or indirectly measuring the current in the split ring resonators or wires or other properties of the split ring resonators or wires.

Moreover, although the illustrative example of a metamaterial included split ring resonators, other types of materials or metamaterials may be incorporated into one or more of the detector assemblies or in addition to the detector assemblies. The selection of the structure of the metamaterial, its properties, such as its effective permittivity, permeability, principal frequency, loss, gain or other aspect is a design choice that may depend upon the intended application, cost constraints, expected input or other design constraints. Similar design considerations apply to the methods and structures for determining the properties of the energy intercepted by the detector assemblies. Further, the field of metamaterials and negative index materials is evolving rapidly and other approaches to forming such materials have been described, including those incorporating transmission lines or wires, nanorods, multiferroic materials, or other approaches to establishing an effective permittivity and/or permeability. In some applications these approaches may be incorporated into one or more of the detector assemblies 102, 106. Although metamaterials have been described as related to electromagnetic radiation, such materials or equivalents to such materials may be implemented for other types of waves. For example, phononic metamaterials have been reported in Suxia Yang, J. H. Page, Zhengyou Liu, M. L. Cowan, C. T. Chan, and Ping Sheng, "FOCUSING OF SOUND IN A 3D PHONONIC CRYSTAL", Physical Review Letters, Volume 93, Page 024301, Jul. 7, 2004, which is incorporated herein by reference.

In one embodiment, the detectors 104, 108 may be quantum dots. One example of how quantum dots may be incorporated as a detector is described in J. L. Jimenez, L. R. C. Fonseca, D. J. Brady, J. P. Leburton, D. E. Wohlert, and K. Y. Cheng, "THE QUANTUM DOT SPECTROMETER", Applied Physics Letters, Volume 71, Number 24, Dec. 15, 1997, page 3558-3560, which is incorporated herein by reference. The quantum dots may be incorporated as detectors 104, 108 in either the first detector assembly 102, the second detector assembly 106, or both. An assembly of quantum dots may comprise a single type of quantum dot that absorbs and re-emits in a relatively narrow wavelength band, or it may comprise more than one type of quantum dot, thus expanding the wavelength band at which the detector assemblies absorb and re-emit.

In another embodiment the detectors 104, 108 may be antennae, where the antennae may include dipole or other types of antennae. Those skilled in the art may recognize that a multitude of different devices may form an antenna and that an antenna may exist in a wide variety of shapes and sizes. For example, an antenna may be very small and include a nanotube, as is described in Y. Wang, K. Kempa, B. Kimball, J. B. Carlson, G. Benham, W. Z. Li, T. Kempa, J. Rybczynski, A. Herczynski, Z. F. Ren, "RECEIVING AND TRANSMITTING LIGHT-LIKE RADIO WAVES: ANTENNA EFFECT IN ARRAYS OF ALIGNED CARBON NANOTUBES", Applied Physics Letters, Volume 85, Number 13, Sep. 27, 2004, which is incorporated herein by reference. The antennae may be incorporated as detectors 104, 108 in one or more of the first detector assembly 102 and the second detector assembly 106. An assembly of antennae may comprise a single type of antenna that absorbs and re-emits in a relatively narrow wavelength band, or it may comprise more than one type of antenna, thus expanding the wavelength band at which the detector assemblies absorb and re-emit.

The signal processor 110 may perform a variety of functions. In one example, where the detectors 104 in the first array are antennae, the processor 110 may extract information from the respective signals from the first detector assembly 102 according to conventional antenna array techniques.

Where the detectors 108 in the second array are antennae, the processor 110 may also extract information from the respective signals from the second detector assembly 106 according to conventional antenna array techniques. Alternatively, where the second detector assembly 106 includes a single antenna, the processor 110 may extract information from the respective signal from the single antenna according to conventional transceiver techniques.

While these illustrative examples involve one or more antenna arrays and application of antenna array or transceiver techniques, the signal processor 110 may apply a range of other techniques in addition to or as an alternative to the previously described techniques. For example, the signal processor 110 may perform a Fourier transform on one or more of the signals for imaging or other purposes, a correlation or autocorrelation between signals, or it may include a filter, which may be a noise filter or other type of filter, and may be low pass, high pass, or bandpass. In one embodiment the source 100 and the detector system 112 may be in motion relative to one another and the signal processor 110 may be configured to compensate for this relative motion.

In one embodiment the signal processor 110 may be configured to sample data from the detectors 104, 108 as a function of time. Such a configuration may be desirable especially in systems where the source 100 and detector system 112 are in motion relative to each other. In this case the sampling rate may be adjustable, and may be determined by the magnitude of the relative motion between the source 100 and the detector system 112.

In one embodiment the signal processor 110 may comprise a computer, wherein the respective signals generated by the first detector assembly 102 or the second detector assembly 106 or a signal corresponding to the respective signals from the first or second detector assemblies 102, 106 is guided to the computer. The computer may comprise software for processing the signals received and it may include one or more devices (not shown) for interfacing the computer and the detector assemblies 102, 106. The computer may or may not be proximate to the first and second detector assemblies 102, 106.

In one embodiment, the signal processor 110 may include components for processing electromagnetic signals. In this case, the signal processor 110 may include components for mixing, reflecting, focusing, or otherwise changing the path of electromagnetic radiation. One example of such a signal processor 110 is an arrangement for heterodyning two signals, in which case the signal processor 110 may include a nonlinear device such as a vacuum tube, transistor, or diode mixer.

Applications of the embodiments described in FIGS. 1-6 are wide ranging and may include imaging and/or image processing, x-ray spectrometry/spectroscopy, radar, medical imaging applications such as PET, CAT scans, MRI, and ultrasound, LIDAR, and other applications.

In one embodiment the subassemblies 104 may be adjustable. The subassemblies 104 may be arranged in a first spatial distribution that is variably responsive, and may be temporally variable. The first spatial distribution may form a portion of a first pattern such that the first pattern is variably responsive, where the first pattern may be temporally variable, and where the first pattern may be variably responsive as a function of the first energy distribution.

In one embodiment at least one of the plurality of subassemblies 104 may include a MEMS device, where the MEMS device may be configured to facilitate adjustment of the one or more subassemblies 104. Although a MEMS device is provided as one exemplary embodiment of a way to adjust the subassemblies 104, other ways of changing the position of elements exist and one skilled in the art may provide other means for adjustment. Further, although a MEMS device may adjust subassemblies 104 having, for example, micron-scale dimensions, in some embodiments the subassemblies 104 may have different dimensions and/or different devices providing adjustment.

In another embodiment at least one of the plurality of adjustable subassemblies is switchable as described, for example, in U.S. patent application Ser. No. 11/355,493, entitled VARIABLE METAMATERIAL APPARATUS, naming Roderick A. Hyde; Nathan P. Myhrvold; Clarence T. Tegreene; and Lowell L. Wood, Jr. as inventors, filed 16 Feb. 2006, which is incorporated herein by reference. For example, depending on the type of subassembly 104, they may be switched on and off, their properties such as dielectric constants may be varied by applying a voltage to them or in another way, and there are many other ways of switching subassemblies 104 depending on the type of subassembly 104.

In one embodiment the first pattern forms a focusing element characterized by a focal distance 304 that is a function of the first energy distribution, such as the zone plate 206 shown in FIG. 2. As described with respect to FIG. 2, the focusing of the arrangement may be dependent on the density of the detectors 104, and in some arrangements, other material may be included in the detector assembly 102 to further define the sections 202, 204. In the case where the first pattern is variable, the pattern may vary to change the effective size of the sections 202, 204, by varying the detectors 104, varying other material that is included in the detector assembly 102, or both. The detectors 104 and/or the other material may be varied by moving them, by changing their properties, by switching them, and/or by other means. In this case the first detector assembly 102 and the second detector assembly 106 may be separated by a separation distance that is variable as a function of the focal distance 304, where the separation between the first detector assembly 102 and the second detector assembly 106 may be configured to vary.

Although the first pattern is described above as forming a zone plate 206, this is just one exemplary embodiment of the first pattern, and there are many other types of elements that may be formed. For example, other diffractive elements exist, such as gratings. Further, the first pattern may form a three-dimensional structure, an array with irregular spacings, or a different pattern.

In one embodiment a first subassembly 104 has a first variable response function and/or a first variable dimension, which may include a first central frequency and/or a first linewidth. Elements having variable response functions and variable dimensions, and methods for varying them are described in VARIABLE METAMATERIAL APPARATUS, previously incorporated by reference.

In one embodiment a first subassembly 104 has a first orientation, wherein the first orientation is variably responsive. In this case the first subassembly 104 may include a MEMS device configured to facilitate the change of the orientation of the first subassembly 104, or the orientation of the subassembly 104 may be varied in a different way. The subassemblies 104 in the first detector array 102 may be configured to be individually variable such that each subassembly 104 may have a different orientation, or the subassemblies 104 in the first detector array 102 may all have the same orientation, where the orientation is adjustable. Further, the subassemblies 104 may be configured such that both their position and orientation are variably responsive, such that the subassembly 104 may be moved and/or rotated. There are many different ways of varying the subassemblies 104 relative to one another and/or relative to a different reference, and one skilled in the art may find different ways and/or combinations of ways of varying the subassemblies 104.

The apparatus may include a signal processor 110 or other electronic circuitry, where the signal processor 110 may be operably connected to at least one of the plurality of subassemblies 104, to receive a signal from the at least one of the plurality of subassemblies 104 and/or to send a signal to the at least one of the plurality of subassemblies 104. The signal processor 110 may be operably connected to the second detector assembly 106, to receive a signal from the second detector assembly 106 and/or to send a signal to the second detector assembly 106. The signal processor 110 may be configured to change the subassemblies 104 in ways described above, for example, to change their relative positions and/or orientations, to switch them, to change their response functions, and/or to change them in another way. The signal processor 110 may further be configured to change the subassemblies 108 in the second detector assembly 106 in any of the ways described for the subassemblies 104 in the first detector array. Further, the signal processor 110 may be configured to change some of the subassemblies 104, 108 in response to others of the subassemblies 104, 108, and/or the signal processor 110 may be configured to change other properties of the detector system 112, such as the separation 114 between detector assemblies, based on information received from the subassemblies 104, 108. There are many ways of modifying the detector system 112 based on feedback obtained from the subassemblies 104, 108, and one skilled in the art may find many applications of varying the detector system 112 based on feedback from the subassemblies 104, 108.

In some embodiments the detector system 112 may include more elements than are shown in FIGS. 1-7. For example, the detector system may include more than two detector assemblies 102, 106. Further, the detector system may include other elements including, but not limited to, filters, polarizers, multiple signal processors, and amplifiers.

Applications of the apparatus described above are wide ranging. For example, the first and/or second detector assemblies 102, 106 may be configured to receive information about the energy distribution of the first wave 101, send this information to the signal processor 110, where the signal processor 101 then adjusts parameters of the detector system accordingly, such as the distribution, position, and/or orientation of the subassemblies in the first or second detector assemblies 102, 106, the separation between the first or second detector assemblies 102, 106, or other parameters.

In another embodiment, the signal processor 110 is configured to perform contrast comparisons between adjacent subassemblies 104 and/or 108 to adjust the position of the subassemblies for optimal imaging, auto-focusing, or for other applications. In still another embodiment, the signal processor 110 is configured to adjust the first and second detector assemblies 102, 106 for spectroscopic imaging, such that the first detector assembly 102 forms a zone plate 206 having a focal distance 304 that is a function of the energy of the first wave 101, and where the separation between the first and second detector assemblies 102, 106 varies (for example, as a function of time) to obtain images at different energies. In another embodiment, the first and/or second detector assemblies 102, 106 include subassemblies 104 and/or 108 responsive to different energies, such that subassemblies 104 and/or 108 having different energy responses may be switched and/or moved as a function of time, for imaging, spectroscopy, or for other purposes.

In one embodiment, adjusting a first detector assembly 102 defines a redistribution pattern that redistributes a waveform (or the first wave 101). The redistributed waveform (or the second wave 105) may be detected at one or more locations defined by the selected redistribution pattern. The first detector assembly 102 may be adjusted by changing a relative position of the first detector assembly 102, with respect to a second detector assembly 106 or another reference.

The energy distribution of the waveform 101 may be measured and the relative position and/or relative orientation of the first detector assembly 102 may be changed accordingly, or the first detector assembly 102 may be switched according to the energy distribution.

The redistributed waveform 105 may be detected with a second detector assembly 106, where the second detector assembly 106 may be adjusted. In one embodiment the second detector assembly 106 is adjusted according to the redistributed waveform 105. Adjusting the second detector assembly 106 may include changing its relative orientation and/or distribution.

Figure 7:
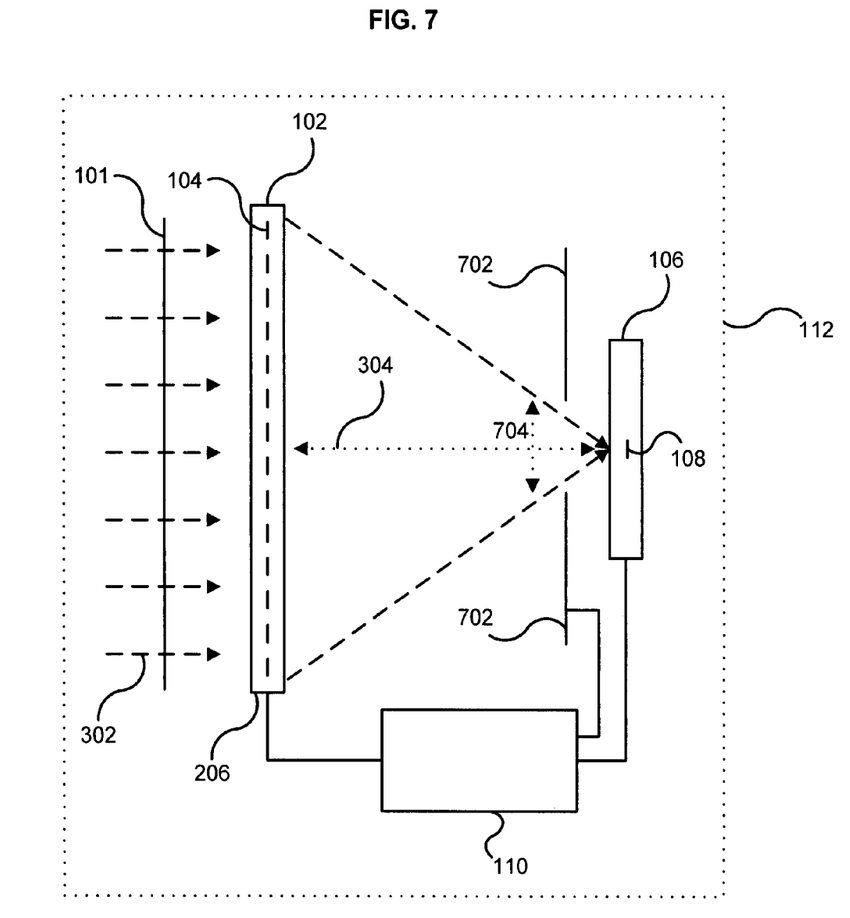
FIG. 7 shows a first embodiment of a detector system including a stop.

In one embodiment shown in FIG. 7 the redistributed waveform 105 is limited with a stop 702 having a stop aperture 704. The stop may be a fixed component or variable component. In some approaches, the stop aperture 704 may be changed independently of other adjustments, or may be adjusted in conjunction with other adjustments to form a composite adjustment.

In one embodiment the first detector assembly 102 includes an array of subassemblies 104 having a distribution, where adjusting the first detector assembly 102 may include changing the distribution of subassemblies 104, or where adjusting the first detector assembly 102 may include changing a relative orientation of at least one subassembly 104 in the array of subassemblies 104.

In one embodiment the first detector assembly 102 is configured to send a signal to a processor 110, and/or the second detector 106 is configured to send a signal to the processor 110.

In one embodiment a system for detecting a waveform comprises a multistage detector (or detector system 112) and a controller (or signal processor 110) operably connected to change the multistage detector 112, wherein the multistage detector 112 includes a first detector array (or first detector assembly 102) arranged to receive a first portion of energy from an incoming wave (or first wave 101) and form a secondary waveform (or second wave 105), and a second detector array (or second detector assembly 106) arranged to receive the secondary waveform 105. The first detector array 102 may have a first spatial distribution, where the controller 110 is operably connected to change the first spatial distribution. The second detector array 106 may have a second spatial distribution, where the controller 110 is operably connected to change the second spatial distribution. The first detector array 102 and the second detector array 106 may have a separation 114, wherein the controller 110 is operably connected to change the separation 114. In one embodiment, the system may include a third detector array, not shown. The controller 110 may be operably connected to receive a signal from the first detector array 102, or from the second detector array 106.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, diagrammatic representations, flowcharts, and/or examples. Insofar as such block diagrams, diagrammatic representations, flowcharts, and/or examples contain one or more functions and/or operations, it will be understood by those within the art that each function and/or operation within such block diagrams, diagrammatic representations, flowcharts, or examples can be implemented, individually and/or collectively, by a wide range of hardware, materials, components, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

Those having skill in the art will recognize that a system may include one or more of a system housing or support, and may include electrical components, alignment features, one or more interaction devices, such as a touch pad or screen, control systems including feedback loops and control motors (e.g., feedback for sensing lens position and/or velocity; control motors for moving/distorting lenses to give desired focuses). Such systems may include image processing systems, image capture systems, photolithographic systems, scanning systems, or other systems employing focusing or refracting elements or processes.

While particular embodiments of the present invention have been shown and described, it will be understood by those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to,"

"comprise" and variations thereof, such as, "comprises" and "comprising" are to be construed in an open, inclusive sense, that is as "including, but not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In one embodiment, an apparatus comprises: a first detector assembly arranged according to a first pattern, said first detector assembly including a plurality of adjustable subassemblies and configured to receive a first portion of energy from a first wave having a first energy distribution and responsive to produce a first signal corresponding to the first portion of the energy; said first pattern further being selected to form a second portion of the energy from the first wave into a second wave having a second energy distribution; and a second detector assembly arranged according to a second pattern, said second pattern being selected according to said second energy distribution and responsive to produce a second signal corresponding to the second portion of the energy.

In some embodiments the second pattern may be variably responsive. In some embodiments the second pattern may be temporally variable. In some embodiments the second pattern may be variably responsive as a function of the second energy distribution. Some embodiments may further comprise a signal processor, wherein the second pattern is variably responsive to a signal from the signal processor.

What is claimed is:

1. An apparatus, comprising:
   a first detector assembly arranged according to a first pattern, said first detector assembly including a plurality of adjustable subassemblies:
      configured to receive a first portion of energy from a first wave having a first energy distribution; and
      responsive to produce a first signal corresponding to the first portion of the energy;
   wherein the plurality of subassemblies are arranged in a first spatial distribution, and wherein the first spatial distribution forms at least a portion of the first pattern;
   said first pattern further being selected to form a second portion of the energy from the first wave into a second wave having a second energy distribution; and
   a second detector assembly arranged according to a second pattern, said second pattern being selected according to said second energy distribution and responsive to produce a second signal corresponding to the second portion of the energy.

2. The apparatus of claim 1 wherein the first spatial distribution is variably responsive.

3. The apparatus of claim 2 wherein the first spatial distribution is variably responsive in a manner that temporally varies at least a portion of the second energy distribution.

4. The apparatus of claim 1 wherein the first pattern is variably responsive.

5. The apparatus of claim 4 wherein the plurality of subassemblies are operative to temporally vary at least a portion of the first pattern.

6. The apparatus of claim 4 wherein the plurality of subassemblies are operative to temporally vary at least a portion of the first pattern as a function of the first energy distribution.

7. The apparatus of claim 1 wherein at least one of the plurality of adjustable subassemblies includes a MEMS device.

8. The apparatus of claim 1 wherein at least one of the plurality of adjustable subassemblies is switchable.

9. The apparatus of claim 1 wherein the first pattern forms a focusing element characterized by a focal length that is a function of the first energy distribution.

10. The apparatus of claim 9 wherein the first detector assembly and the second detector assembly are separated by a separation distance that is variable as a function of the focal length.

11. The apparatus of claim 1 wherein a first subassembly has a first variable response function.

12. The apparatus of claim 11 wherein the first variable response function includes a first central frequency.

13. The apparatus of claim 11 wherein the first variable response function includes a first linewidth.

14. The apparatus of claim 1 wherein a first subassembly has a first orientation, and wherein the first orientation is variably responsive.

15. The apparatus of claim 14 wherein the first subassembly includes a MEMS device.

16. The apparatus of claim 1 wherein a first subassembly has a first variable dimension.

17. An apparatus, comprising:
   a first detector assembly arranged according to a first pattern, said first detector assembly including a plurality of subassemblies configured to receive a first portion of energy from a first wave having a first energy distribution and responsive to produce a first signal corresponding to the first portion of the energy;
   said first pattern further being selected to form a second portion of the energy from the first wave into a second wave having a second energy distribution;
   a second detector assembly arranged according to a second pattern, said second pattern being selected according to said second energy distribution and responsive to produce a second signal corresponding to the second portion of the energy; and
   a signal processor operably connected to the apparatus to modulate at least one of the first detector assembly, the first pattern, and the second detector assembly.

18. The apparatus of claim 17 wherein the signal processor is operably connected to at least one of the plurality of subassemblies.

19. The apparatus of claim 18 wherein the signal processor is operably connected to at least one of the plurality of subassemblies to receive a signal from the at least one of the plurality of subassemblies.

20. The apparatus of claim 18 wherein the signal processor is operably connected to at least one of the plurality of subassemblies to send a signal to the at least one of the plurality of subassemblies.

21. The apparatus of claim 17 wherein the signal processor is operably connected to the second detector assembly.

22. The apparatus of claim 21 wherein the signal processor is operably connected to the second detector assembly to receive a signal from the second detector assembly.

23. The apparatus of claim 21 wherein the signal processor is operably connected to the second detector assembly to send a signal to the second detector assembly.

24. The apparatus of claim 17 wherein the first pattern is variably responsive to a signal from the signal processor.

25. An apparatus, comprising:
a first detector assembly arranged according to a first pattern, said first detector assembly including a plurality of subassemblies configured to receive a first portion of energy from a first wave having a first energy distribution and responsive to produce a first signal corresponding to the first portion of the energy;
wherein the plurality of subassemblies are arranged in a first spatial distribution, and wherein the first spatial distribution forms at least a portion of the first pattern;
said first pattern further being selected to form a second portion of the energy from the first wave into a second wave having a second energy distribution;
a second detector assembly arranged according to a second pattern, said second pattern being selected according to said second energy distribution and responsive to produce a second signal corresponding to the second portion of the energy; and
wherein the second pattern is variably responsive.

26. The apparatus of claim 25 wherein the second pattern is temporally variable.

27. The apparatus of claim 25 wherein the second pattern is variably responsive as a function of the second energy distribution.

28. The apparatus of claim 25 further comprising a signal processor, wherein the second pattern is variably responsive to a signal from the signal processor.

* * * * *